United States Patent [19]
Gohla et al.

[11] Patent Number: 5,096,708
[45] Date of Patent: Mar. 17, 1992

[54] MEDICAL PREPARATION CONTAINING AS ACTIVE AGENT A COMPONENT FROM THUJA PLANTS WHICH COMPRISES POLYSACCHARIDES

[76] Inventors: Sven Gohla, Waitzstr. 17, Hamburg 52, Fed. Rep. of Germany, 2000; Rolf D. Neth, Pennskuhle 9, Buchholz, Fed. Rep. of Germany, 2110; Hans D. Haubeck, Muffeterweg 52, Aachen, Fed. Rep. of Germany, 5100

[21] Appl. No.: 363,257

[22] Filed: Jun. 8, 1989

[30] Foreign Application Priority Data

Jul. 7, 1988 [DE] Fed. Rep. of Germany ....... 3822945
Nov. 4, 1988 [EP] European Pat. Off. ....... EP88118394

[51] Int. Cl.$^5$ .............................................. A61K 35/78
[52] U.S. Cl. ................................... 424/195.1; 514/54
[58] Field of Search ........................ 424/195.1; 514/54

[56] References Cited

U.S. PATENT DOCUMENTS 4,716,120 12/1987 Tsay et al. ........................... 436/513

Primary Examiner—Jose G. Dees
Assistant Examiner—Vera C. Clarke
Attorney, Agent, or Firm—Nixon & Vanderhye

[57] ABSTRACT

A medicament is described which contains as the active substance a component which is obtained from thuja plants and contains polysaccharides.

A specific induction of the lymphocyte T-helper cell fraction of the peripheral blood is obtained with the plant component. The specific induction of the fraction of T-helper cells is connected with the expression of the T-helper cell activation labels Okt 17 and Okt 26a as well as an increased interleukin-2 synthesis.

The component according to the invention also stimulates the formation of leukocytes and exercises a protective effect against the damages caused by radioactive radiation.

4 Claims, 14 Drawing Sheets

TIME AND DOSE-DEPENDENCE OF THE MITOGENETIC EFFECT OF TPS

BIOLUMINESCENCE TEST

PHAGOCYTOSIS ASSAY FOR NEUTROPHILIC GRANULOCYTES

PHAGOCYTOSIS ASSAY FOR NEUTROPHILIC GRANULOCYTES
TARGET CELLS - CANDIDA ALBICANS

TPS DOES NOT HAVE A MITOGENIC EFFECT ON CONCENTRATED B CELLS

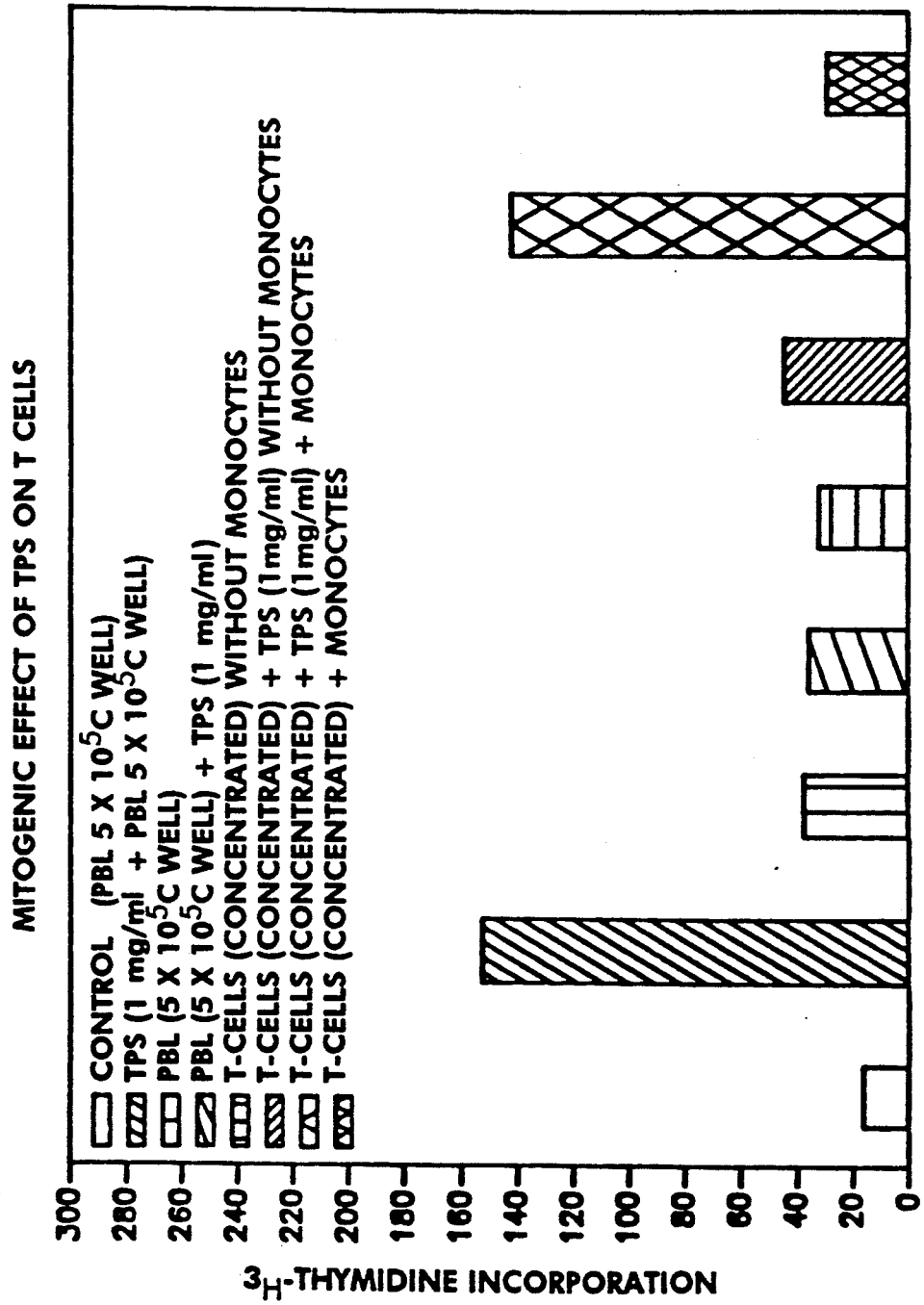

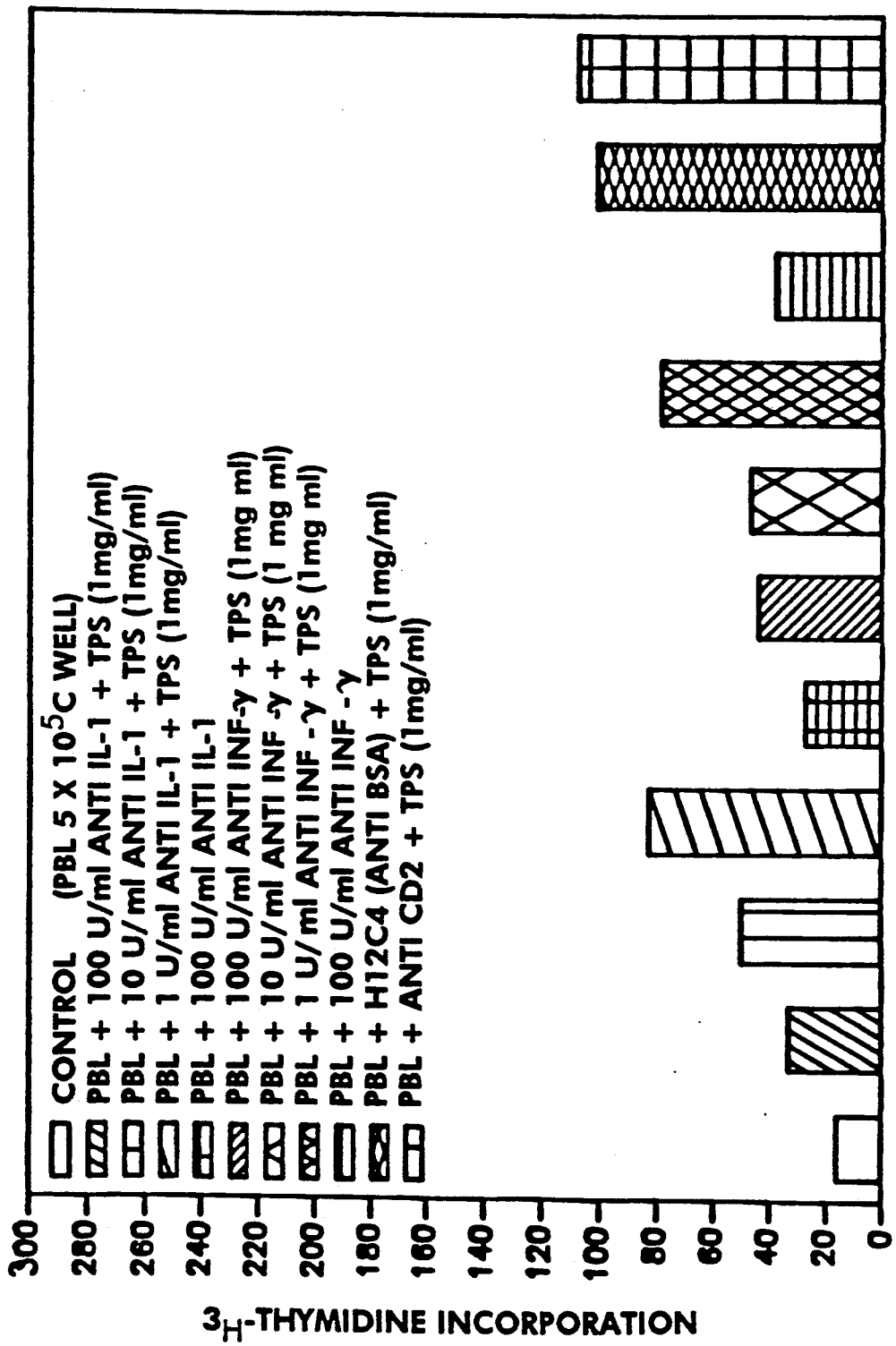

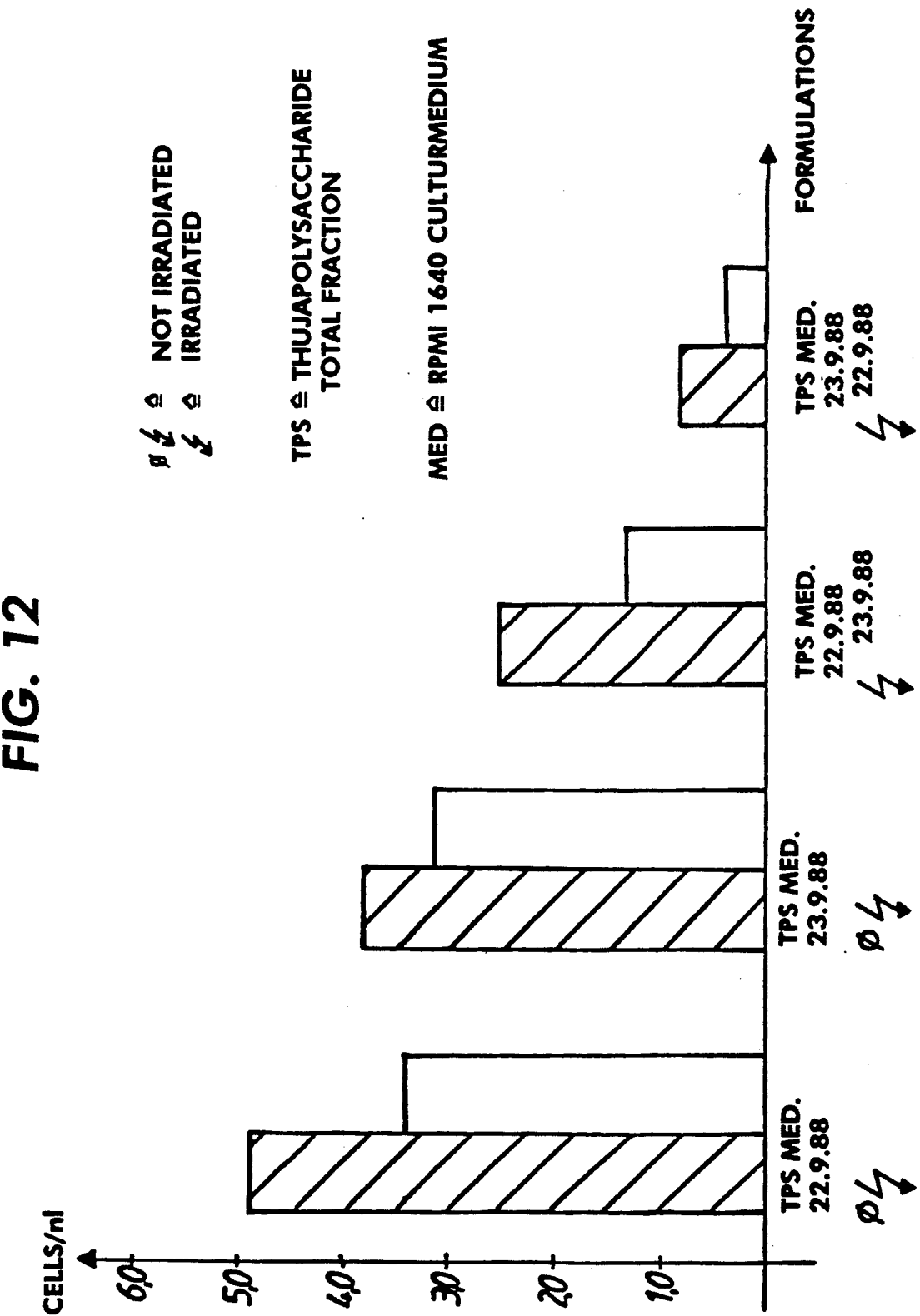

13A
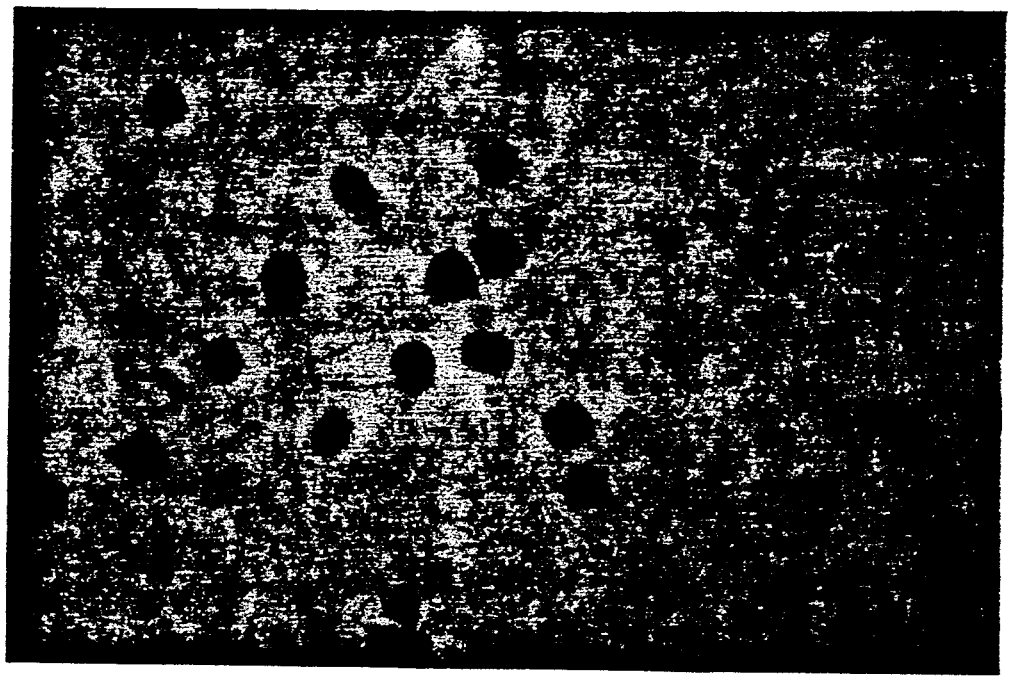
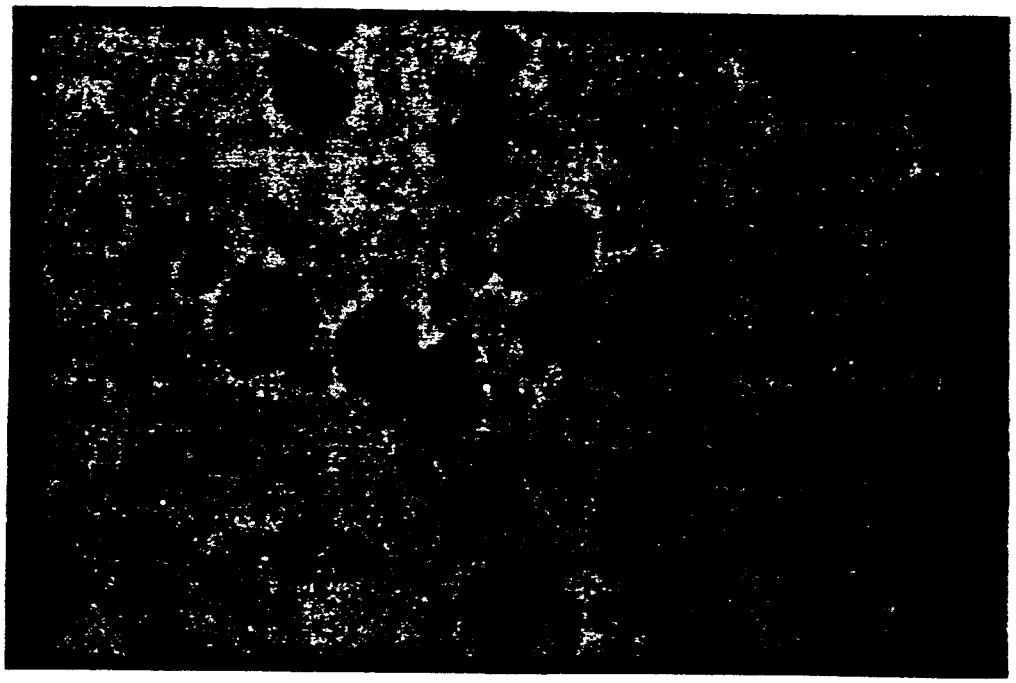
13B

14 A
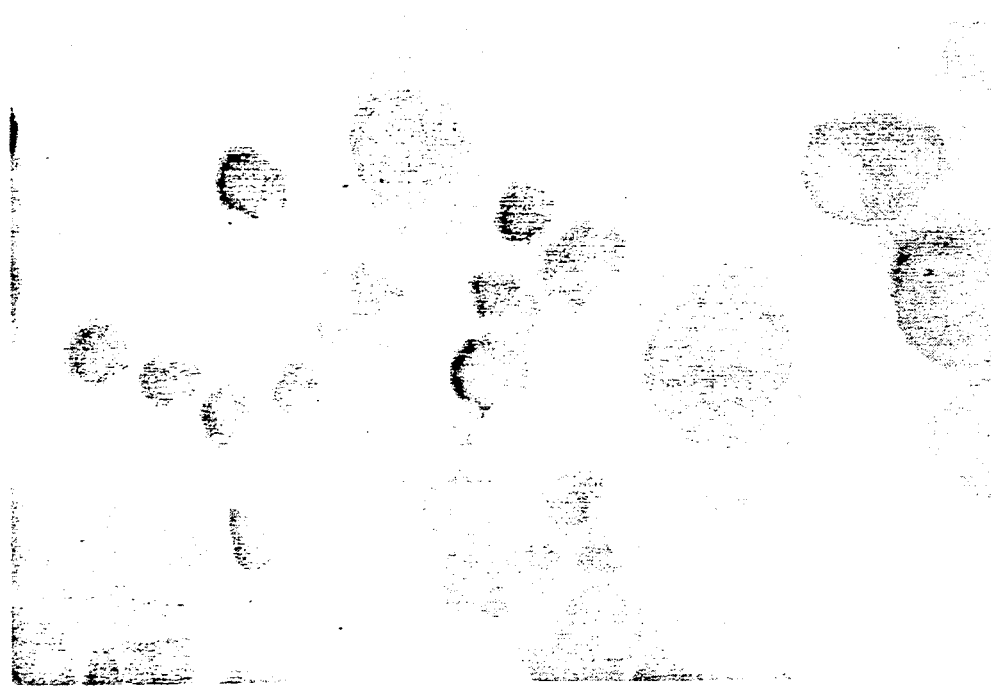
14 B

MEDICAL PREPARATION CONTAINING AS ACTIVE AGENT A COMPONENT FROM THUJA PLANTS WHICH COMPRISES POLYSACCHARIDES

The invention relates to a component from thuja plants, in particular from *Thuja occidentalis L.*, which contains polysaccharides, and which has an immunoregulatory effect especially on the specific immune systems of mammals and humans.

BACKGROUND OF THE INVENTION

The influence of lymphocytic immunoregulation by plant extracts was until now only possible in the form of unspecific polyclonal lymphocyte stimulation by, for example, the group of substances known as lectins, i.e. proteoglykanes with a mitogenic effect. However, the high toxicity of the lectins has proved disadvantageous and makes an in vivo application of these substances impossible.

Furthermore, polysaccharide fractions particularly from Asteraceae drugs have been described which were obtained from an aqueous or aqueous-alkaline extract, (cf. Wagner et al., Arzneimittelforschung, 35, 1069 to 1075 (1985)). These polysaccharide fractions showed an unspecific increase in granulocyte and monocyte or macrophage phagocytosis. A weak polyclonal stimulation of B-and T-lymphocyte fractions was also observed in the polysaccharide isolated from *Echinacea curpurea* (EPS), cf. Wagner et al., angewandte Phytotherapie 2, 166 (1981). A polyclonal stimulation of micro- and macro-phagocytes can also be achieved with the polysaccharide described.

Previously no polysaccharide from higher plants has been described, which causes a selective stimulation of lymphoid and/or myeloid cell fractions.

In the same way until now a selective influence of specific lymphocytic subpopulations, such as for example T-helper cells, was not possible to an extent corresponding to the present level of research with a component from higher plants and containing polysaccharides.

It is therefore an object of the invention to produce a medicament for the treatment of diseases which involve immune system disorders, such as is the case for example with the Di-George-syndrome and with AIDS.

It is a further object of the invention to provide a new medicament for the reconstitution of bone marrow following, for example, the effects of ionizing radiation or cytostatic therapy.

It is a particular object of the invention to provide a therapeutic medicament for patients with HIV-infections, which, while selectively reconstituting the T-helper cells, simultaneously brings about a reduction of the HTLV IIIb virus which is causing the illness.

The medicament according to claim 1 is proposed to achieve these objects. Claims 2 to 6 relate to preferred embodiments of the invention.

BRIEF DESCRIPTION OF THE DRAWINGS

FIG. 10 is a bar graph showing that T-lymphocytes are selectively stimulated in the presence of monocytes or macrophages as discussed in Example 8;

FIG. 11 is a bar graph showing that the effect of TPS on PBL can be reduced by high doses of anti-IL-1 and anti-$\mu$-IFN as discussed in Example 10;

FIG. 12 is a bar graph showing the in vitro regulatory effect of TPS on BALB-C-inbred mice to compare the effects of radiation on leukocyte count with and without TPS as described in Example 11;

FIGS. 13A and 13B are micrographs showing the selective activity of TPS on T-helper cells using Pappenheim-staining as described in Example 4. FIG. 13A shows the stained unstimulated cells; FIG. 13B shows the stained cells stimulated with TPS; and FIGS. 14A and 14B are micrographs showing the selective activity of TPS on T-helper cells using the APAAP process as described in Example 4. FIG. 14A uses T cell negative antibodies and FIG. 14B used T cell positive antibodies.

DESCRIPTION OF THE INVENTION

Figure 1:
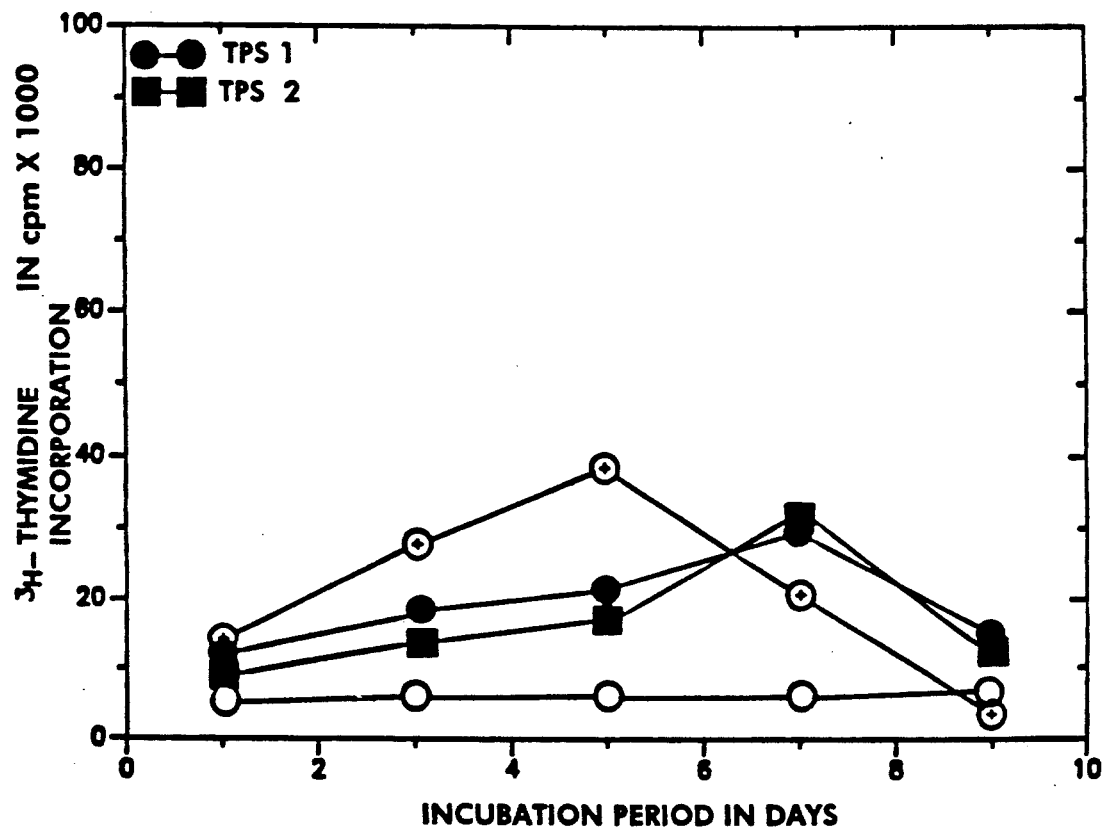
FIG. 1 is a graph showing the mitogenic activity on peripheral human blood lymphocyte (PBL) as determined in Example 3 of TPS-1 and TPS-2 subfractions prepare din Example 1 and isolated in Example 2 compared to a control of Dulbeco's modified Eagle's medium (DME) and phythaemagglutinin (PHA) by measuring $^3$H-thymidine incorporation over a period of days.

According to the invention it has surprisingly been found that a component from thuja plants, in particular from *Thuja occidentalis L.*, which contains polysaccharides has a mitogenic effect on T-helper lymphocytes. This effect is particularly marked in fractions of the component with a molecular weight of more than 100,000 D (see Example 4).

The effect according to the invention on the subgroup of T-helper cells with receptors for the monoclonal antibodies Okt$^R$4 and Okt$^R$17 (cf. Ortho-mune$^R$, monoclonal antibodies, "Zur Typisierung immunologischer aktiver Zellen") is selective (for the general characterization of white blood corpuscles cf. also Reinherz, E.L., Schlossman, S.F., "The Differentiation and Function of Human T-lymphocytes, Cell 19, 821 to 827 (1980) and Reinherz, E.L., et al., Leukocyte typing II, Volume 3, "Human myeloid and hemapoietic cells", Springer Verlag, (1986)).

Unlike the polysaccharide fractions described in the prior art from higher plants other than thuja, and in particular the Asteraceae drugs *Echinacea angustifolia* and purpurea, the components containing polysaccharides which are isolated from thuja according to the invention cause a specific induction of the T-helper cells.

The mitogenic effect of the components according to the invention is dependent on the presence of autologous monocytes or macrophages. It can also be inhibited by anti-interleukin-1 and anti-interferon-gamma antibodies. The selective mitogenic effect of the thuja component (TPS) is linked to an increased $^3$H-thymidine incorporation rate, which reaches its proliferation maximum after 7 days incubation.

The T-helper cells induced by TPS express the surface labels $Okt^R4$, the surface label for T-helper cells; $Okt^R17$, a surface label for the activated helper cells and $Okt^R26a$, the interleukin-2 receptor (for the characterization of the surface labels cf. loc. cit.). A TPS-induced increased production of the lymphokine interleukin-2 was furthermore observed in the invention.

In addition it has surprisingly been found that the thuja component according to the invention causes a reduction in the replication and the infectious nature of lenti- and retroviruses towards healthy white blood cells in vertebrates with a simultaneous induction of T-helper cells.

Finally, it has surprisingly been found that the thuja component according to the invention is able to stimulate leukocyte formation and to develop a protective effect against the damages caused by radioactive radiation (see Example 10).

The thuja component containing polysaccharides according to the invention can be produced from above-ground thuja plant parts, and preferably from *Thuja occidentalis L.*, following the method according to Caldes et al., J. Gen. Appl. Microbiol. 27, 157 ff. (1981).

For this purpose the plant parts are first reduced in size, for example by grinding. After this a preextraction is preferably carried out with organic solvents such as petroleum ether, dichloromethane and/or methanol, in order to disintegrate and clean the material.

The residue is dried and is subsequently subjected to the actual extraction process, in which it is extracted at 1° to 10° C., preferably at 2° to 6° C., with an aqueous alkaline solution. Preferably 0.1 to 1.0N and in particular 0.5N aqueous NaOH-solution is used for the extraction. The extract is filtered and then precipitated with alcohol, preferably with ethanol, an ultimate ratio of ethanol : water of approximately 3 : 1 being preferred.

The precipitate can be separated off for example by ultracentrifugation and subsequently dissolved in water.

In the next stage the proteins are precipitated in a known manner by acidification of the solution, for example with trichloroacetic acid. After separation of the residue the supernatant is again treated with ethanol to obtain the component containing polysaccharides of the invention.

In the described process hemicelluloses are essentially obtained. The substance obtained is taken up in water, dialyzed for example through a dialysis tube with a separation limit of 100 dalton and then dried, preferably freeze-dried. The product obtained (TPS) is essentially free of proteins and nucleotides.

For further separation TPS can be transferred into an aqueous solution and sub-divided by ultrafiltration into fractions according to molecular weight.

It has been shown in the invention that both the total fraction of TPS with a molecular weight of at least 100 D and the TPS sub-fractions have the activity according to the invention with the activity being observed preferably in fractions with a molecular weight of at least $1 \times 10^5$D (see example 3).

Surprisingly it has additionally been shown that the component from thuja plants, which contains polysaccharides, according to the invention does not have any in vitro toxic effect even in high doses.

In in vitro experiments with human peripheral blood cells it has been shown that the optimum effect is achieved with active substance concentrations of approximately 0.1 to 1 mg/ml of aqueous solution (see Example 3), the fractions with a higher molecular weight having a higher specific activity.

The component from thuja plants TPS according to the invention can be used as the active substance in medicaments, fractions with a molecular weight of at least $1 \times 10^5$D preferably being used to produce the mitogenic effect.

The active substance from thuja plants according to the invention can be manufactured into medicaments with the usual carrier and auxiliary substances, provided that the latter are suitable for the form of application and are pharmaceutically safe. TPS is preferably administered by parenteral route in physiological saline solution.

The invention is further demonstrated in the following by the examples.

EXAMPLE 1

Production of the component according to the invention

Processing of the drug (plant parts):

The dried and ground drug was subjected to a depleting Soxhlett extraction with petroleum ether, dichloromethane and methanol. The drug thus pre-extracted was dried in air for further processing.

Obtaining the raw polysaccharides from an aqueous-alkaline extract:

All the steps, if not otherwise stated, were carried out at 4° C.

800 g of the dried pre-treated medicament (see above) was mixed with 10 liters of a 0.5N NaOH and stirred overnight.

The residue was centrifuged off, washed with 5 liters of 0.5 NaOH and the combined filtrates mixed slowly with constant stirring with three times the volume of 96% ethanol (not denatured). The precipitate formed overnight was then carefully decanted and finally separated off from the remaining supernatant by ultra-centrifugation (15,000/rpm, t=15 min).

The precipitate thus obtained was dissolved in 3.5 l distilled water and slowly mixed in an ice bath with 3.5 liters of 15% trichloroacetic acid (TCA) and left for an hour in the ice bath. After this the jelly-like residue was centrifuged off and the remaining supernatant, approx. 6 liters, was divided into 3 liter fractions and each mixed dropwise with 12 liters of 96% ethanol. After 24 hours the precipitate formed from both fractions was centrifuged off, combined and taken up in as little as possible of 2% sodium acetate solution. The insoluble constituents were centrifuged off (10,000 g. t=20 min).

The clear solution was mixed with 8 liters of 96% ethanol and the precipitate was left for 4 days at 4° C. This was then centrifuged off, the raw polysaccharide formed was dialyzed for 96 hours against distilled water (dialysis tube, separation boundary 100 D, approx. 4° C.) and then lyophilized.

Yield: 15.66 g raw substance = 1.9%

Purification 10 g of the raw polysaccharide was dissolved in 500 ml of distilled water. The solution was added to 500 ml of 96% ethanol dropwise and with constant stirring at 4° C.

The precipitate was centrifuged off after 4 days (15,000 rpm, 10 min) and the supernatant was mixed with the same amount of ethanol in the same manner and treated further.

The process was repeated with four times the volume of ethanol.

The precipitates were taken up in a small amount of distilled water, dialyzed and then freeze-dried.

Starting substance: 10 g of drug

TPS yield: 1:1 precipitation: 8.76 g corresponding to 87.60% TPS, based on the raw substance TPS yield: 1:4 precipitation: 0.767 g corresponding to 7.67% TPS based on the raw substance

EXAMPLE 2

Isolation of Subfractions of TPS

The isolation of subfractions was carried out by ultrafiltration. TPS as in Example 1 was dissolved in distilled water to a concentration of 2 mg/ml. 100 ml of the solution was continuously filtered in an ultra-filtration cell (Ultra Sart 50, Sartorius, Germany) under a nitrogen pressure of 1.5 bar.

The filter types listed below were used here. All the filter types used were obtained from the Sartorius Company.

| SM 113 28 | >1000,000D |
| SM 113 18 | >300,000D-<1000,000D |
| SM 146 69 | >100,000D-<300,000D |
| SM 149 49 | >20,000D-<100,000D |

The subfractions thus obtained were dialyzed for 48 hours against re-distilled water and then lyophilized.

| Yield: | | |
| --- | --- | --- |
| TPS 1, mol. weight | >1000,000D | 5.45 g |
| TPS 2, mol. weight | >300,000D-1000,000D | 1.42 g |
| TPS 3, mol. weight | >100,000D-<300,000D | 0.74 g |
| TPS 4, mol. weight | >20,000D-<100,000D | 0.53 g |
| TPS 5, mol. weight | <20,000D | 0.25 g |

Dialyses

The dialyses were carried out using a dialysis hose (Union Carbide: Dialysis membrane, 1-8×100FP) or a dialysis tube (Asahi Medical AM-100H). For the dialysis in the dialysis tube the material to be dialyzed was pumped through the tube continuously by means of a hose pump. The dialysis fluid (distilled water) was also passed continuously through the tube at the water inlet and outlet nozzles of the dialysis tube by means of a water-jet pump (p not > 1.5 bar). Owing to the high separation efficiency of these dialysis tubes it was possible to limit the dialyses to 10 hours.

All the sub-fractions together with the total-TPS were tested according to standard procedures for the presence of nucleotides and proteins. The results showed that neither proteins nor nucleotides were present in detectable amounts.

The Carbozole test (cf. Nature 1948, 483) was used to determine acidic polysaccharides. For this purpose reference series of 5 to 40 μg of galacturonic acid and glucuronic acid-gamma-lactone were produced.

The samples to be tested were treated with $H_2SO_4$ and extinction determined. An uronic acid content of about 5% was found based on the reference series.

EXAMPLE 3

Determination of the mitogenic activity of TPS and TPS 1 to 4

TPS and the sub-fractions TPS 1 to 4 were dissolved in "Dulbecco's modified Eagle's medium (DME)" +10% human AB-serum. The active substance concentration was 10 mg/ml for each.

An active-substance dilution series of 5 mg/ml to 100 ng/ml was prepared. Peripheral human blood lymphocytes (PBL) were concentrated through a polysaccharose gradient (Ficoll-Paque, Pharmacia), washed 5 times with phosphate-buffered saline solution (0.9%) kept at a temperature of 37° C., taken up in DME + 10% AB-serum and distributed in a cell density of 5 × $10^5$ cells in 100 ul/microtitre well in a 96-well flat-bottomed microtitre plate (Greiner Company).

The test solutions were analysed in triplicate in the endconcentrations given above. Incubation took place in a Heraeus incubator at 37° C., 5% $CO_2$ and 100% air humidity. 100 ul DME + 10% AB-serum was used as negative control and as the positive control a lectin solution of Phaseolus spp., known as phythaemagglutinin, (PHA), adjusted to an end concentration of 10 μg/ml, was used.

This test formulation was used in all the tests for mitogenic activity, the following incubation step beeing additionally implemented for the determination of the TPS induced DNS-synthesis for TPS and the control cultures described: Per microtitre well in an end-concentration/well from 0.2 to 1.5 μCi $^3$H-thymidine was added and incubated for 12 hours in the incubator. Subsequently the radiolabelled cells were drawn on to a filter paper with a cell-harvesting device (Scatron cell harvester) and the radioactivity determined as cpm (counts per minute) by adding a scintillation cocktail (POPPOP).

The results are reproduced in FIGS. 1 to 4. They show the mitogenic activity of TPS and TPS 1 to 4 on PBL.

EXAMPLE 4

The selective activity of TPS on T-helper cells was shown by staining using the APAAP-process (alkaline phosphatase anti-alkaline phosphatase-staining, Erber et al., Lanceti, 1042 ff.). First it was shown using Pappenheim-staining (May Gruenwald Giemsa dye) that the cells stimulated by TPS were in fact lymphoblasts (see FIGS. 13A and 13B). The APAAP-staining enabled a selective distinction to be made in the second stage between the lymphocyte and monocyte subpopulations and thus also enabled categorization of the agent's effect on specific cell fractions (see FIGS. 14A and 14B).

Haematoxylin nucleus staining was used as a comparative staining method with the APAAP-staining.

For staining, the cells which had been cultivated under the conditions in Example 3, were harvested from the microtitre wells with an Eppendorf pipette and fixed on a slide by Cytospin. Some of these cells underwent Pappenheim staining to establish which basic type (monocytic or lymphocytic series) of cells were induced by TPS. The others were examined by means of the APAAP method for specific lymphocytic cell labels. The following antibodies were used:

| For T-cells: | anti Okt$_3$ (anti-CD$_3$); anti Okt$_{11}$ (anti-CD$_2$); anti Okt$_4$ (anti-CD$_4$) and anti Okt$_8$ (anti-DC$_8$). |
|---|---|
| For B cells: | OKB$_{22}$ (anti-CD$_{22}$) |

Figure 2:
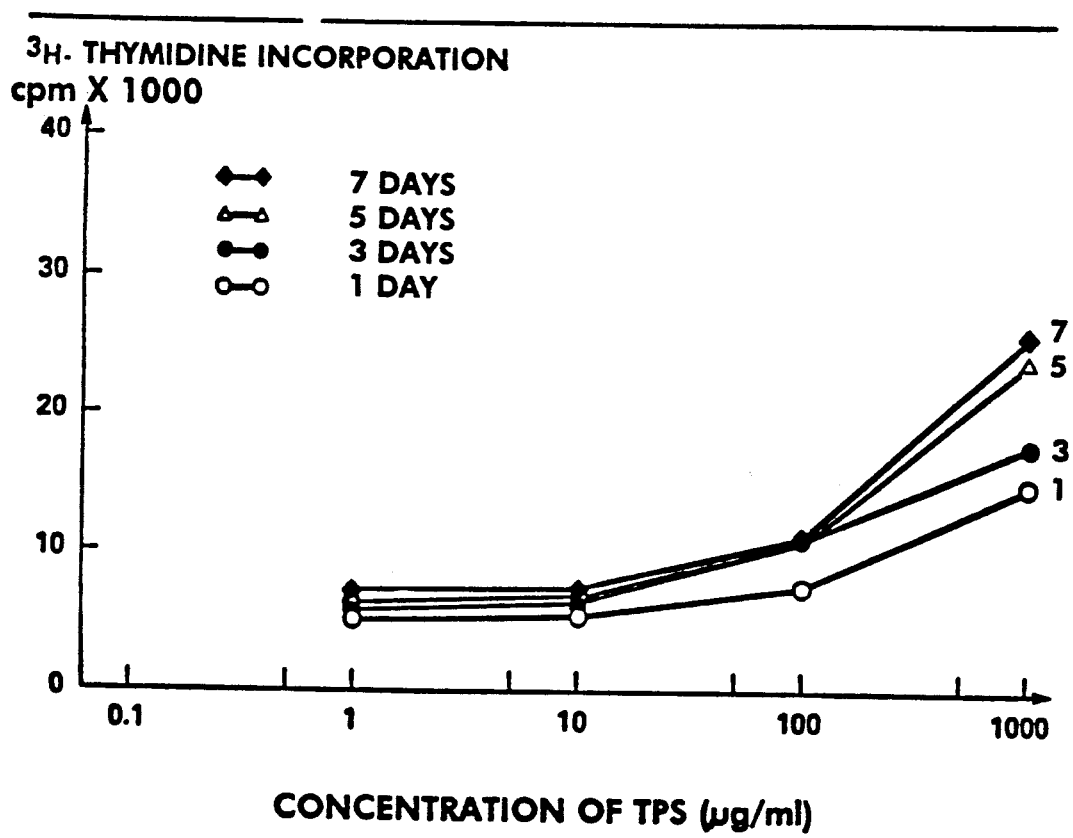
FIG. 2 is a graph showing the time and dose dependence of the mitogenic effect of TPS by measuring $^3$H-thymidine incorporation against TPS concentration for periods of 1, 3, 5 and 7 days.
Figure 3:
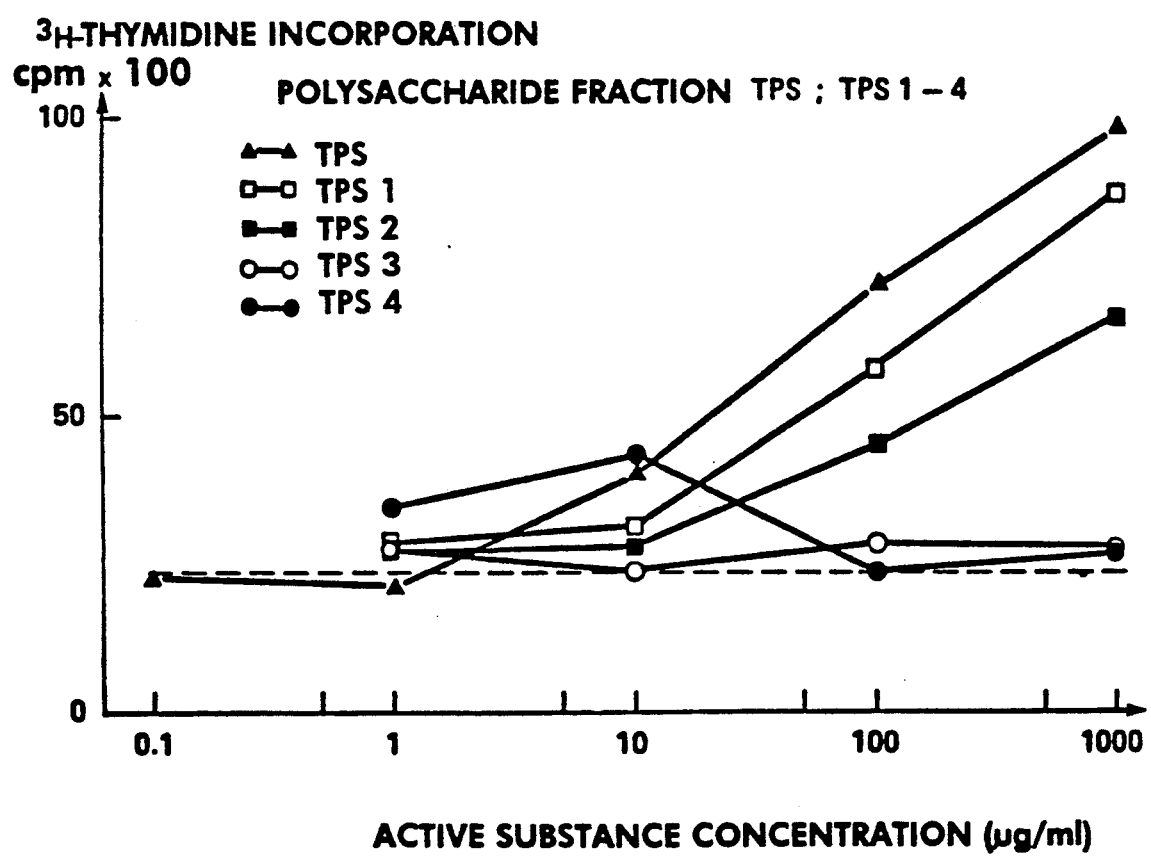
FIG. 3 is a graph showing the mitogenic activity of the polysaccharide fractions of TPS and TPS 1-4 by measuring $^3$H-thymidine incorporation against various concentrations of the active substance.
Figure 4:
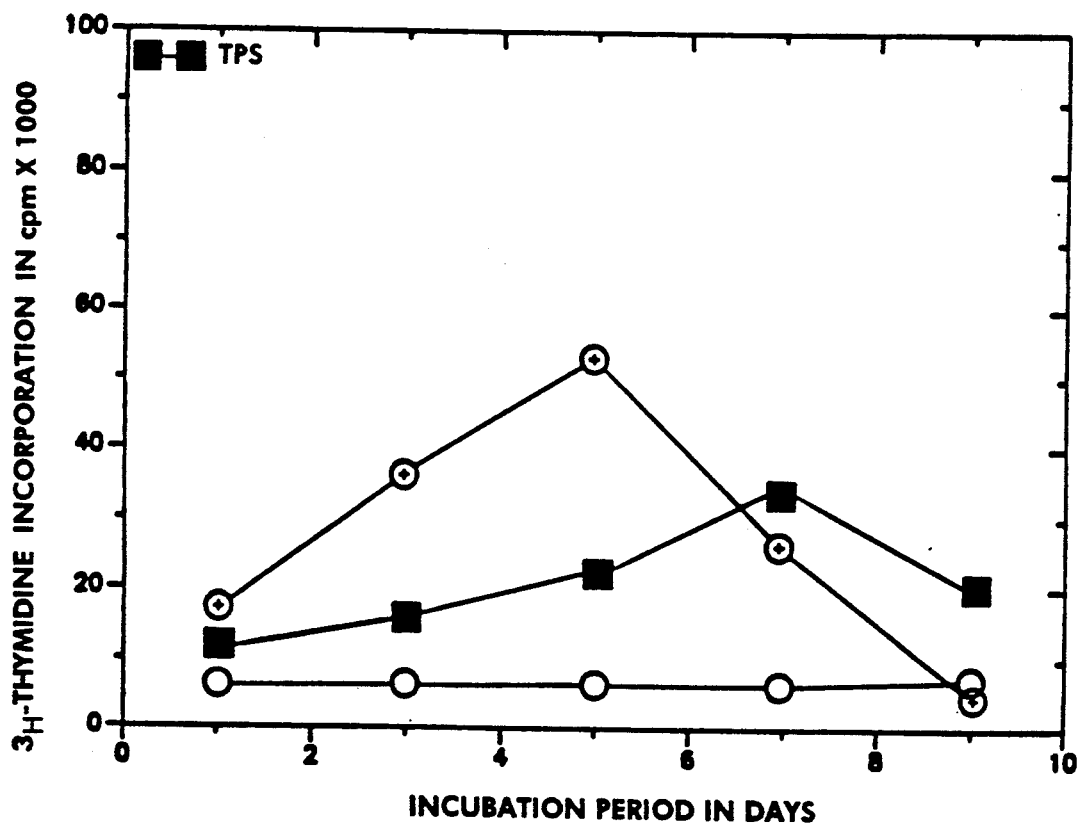
FIG. 4 is a graph showing the mitogenic activity of TPS compared to a control (DME) and PHA as in FIG. 1.

The results are reproduced in FIGS. 1 and 2. They show that TPS stimulates the lymphoblastoid cells to proliferation (FIG. 1) and among these selectively stimulates the CD$_4$-positive T cells (FIG. 2).

EXAMPLE 5

Activation of the natural killer cells' response

Production of a cell suspension from spleens:

Mice of the strain BALB/C were killed by cervical dislocation. Their spleens were removed in sterile conditions and pulled to pieces with surgical pincers in a Petri dish (Greiner, Nuertingen) which was filled with 10 ml of BSS (pH-stabilized saline solution).

To obtain a single cell suspension the cells were rinsed out of the tissue fragments by pipetting in and out with a Pasteur pipette. The suspension was filtered through a sterile wire gauze to remove tissue residue.

The cells thus prepared were washed 5 times with BSS (200 g, 10 min., Minifuge, Heraeus, Osterode).

The effect of TPS on the induction of natural killer cells was assessed by the chromium 51 liberation test.

Production of the target cells:

The spleen cells were prepared as described. YAC-1, a mouse fibrosarcoma, is an excellent NL-target cell. The cells were washed 3 times with BSS and adjusted to about $5 \times 10^6$ cells. This number of cells was incubated for 1 hour at 37° C. with 0.1 ml Na$^{51}$CrO$_4$ (37,000 kilobecquerel/ml, Amersham Buchler, Braunschweig), then washed 3 times with BSS and adjusted to $4 \times 10^5$ cells/well. These cells were plated out in 100 μl stages in 96-well flat-bottomed microtitre plates.

Chromium liberation

In a microtitre plate different amounts of effector cells which were previously incubated for 6 or 18 hours with different concentrations of TPS were added to the target cells. (100:1; 50:1; 25;1; 12.5:1.; 1 mg/ml–100ng/ml).

The ultimate volume of the culture was 0.2 ml. The maximum Cr$^{51}$- liberation was determined by total cell lysis indicated by sodium hydroxide solution (1M, Merck). The target cells alone gave the value for spontaneous liberation. The cells were incubated for 6 and 18 hours in the incubator at 37° C.

Determination 0.1 ml was removed from each batch and the radioactivity contained therein measured in the gamma-ray counter.

The lytic activity of the effector cells was calculated as % of chromium liberation according to the following formula:

$$\% \text{ specific lysis} = \frac{\text{cpm test formulation} - \text{cpm spontaneous liberation}}{\text{cpm max. liberation} - \text{cpm spontaneous liberation}} \times 100$$

Figure 5:
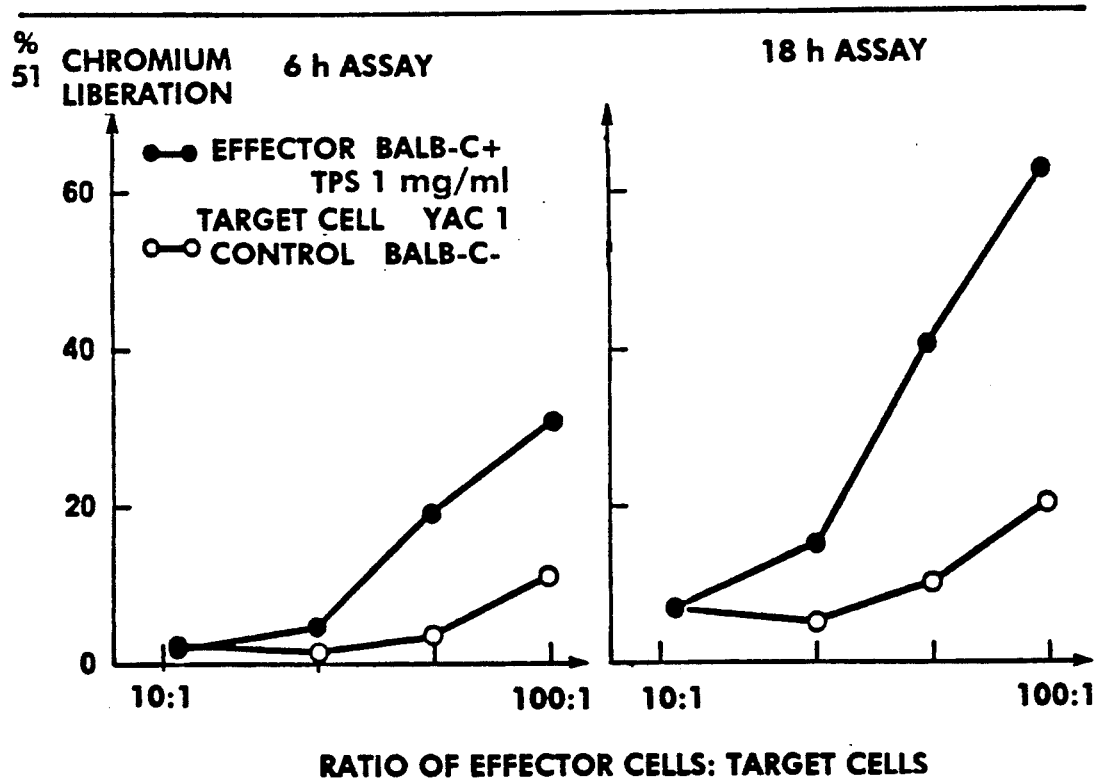
FIG. 5 is a graph depicting the results of the NK-cell assay of Example 5 showing an increase in killer cell activity against YAC-1-target cells under the influence of TPS.

The results are reproduced in FIG. 5. They show the increase in killer cell activity against YAC-1-target cells under the influence of TPS.

EXAMPLE 6

The increase in granulocyte phagocytosis caused by TPS was determined according to Allen (cf. Allen L.C. et al, Biochem. Biophys. comp. Res. Immun. 47, 679).

Figure 6:
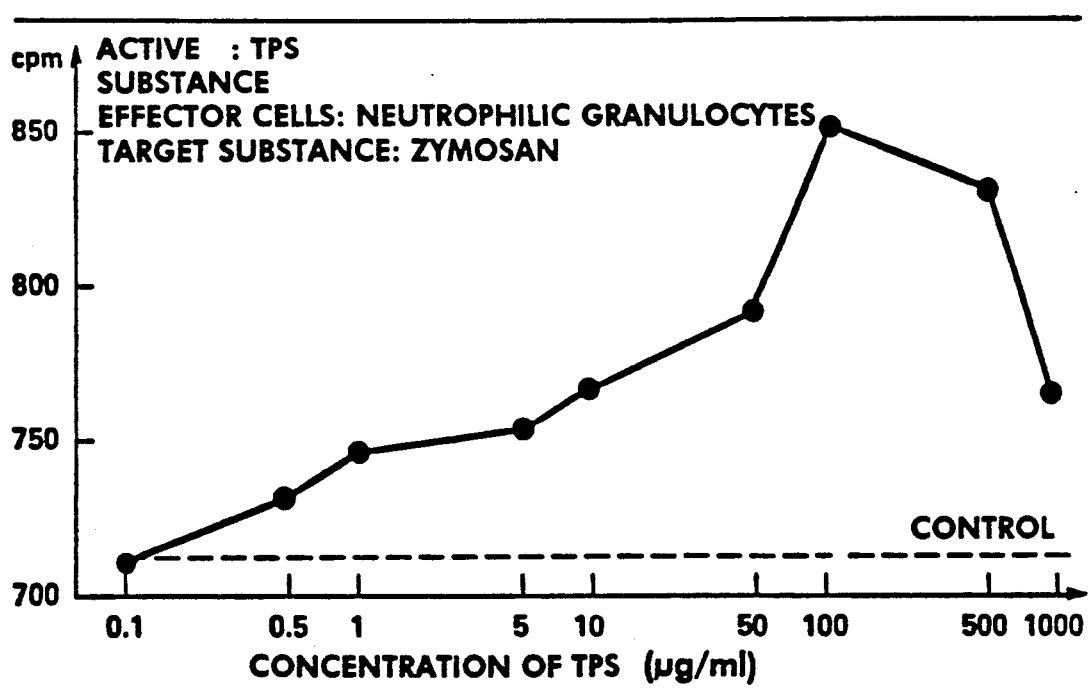
FIG. 6 is a graph showing an increase in phagocytosis of neutrophilic granulocytes for Zymosan under the influence of TPS using the bioluminescence test of Example 6.

The results are reproduced in FIG. 6. They show the increase in the phagocytosis of neutrophilic granulocytes for Zymosan under the influence of TPS, the optimum effect lies at 100 μg/ml.

The granulocyte phagocytosis assay according to Brandt, Scand. J. Haemotol. Suppl., 2 (1967) for the panoptic evaluation of granulocyte phagocytosis was introduced as the second reference method. Whole living cells of *Candida albicans* were used as the target substance. Both methods agreed in showing the increase in phagocytosis of neutrophilic granulocytes under the influence of TPS and of the sub-fractions TPS1 and TPS2, and the optimum activity for each lying at 100 μg polysaccharide concentration/reaction vessel.

Figure 7:
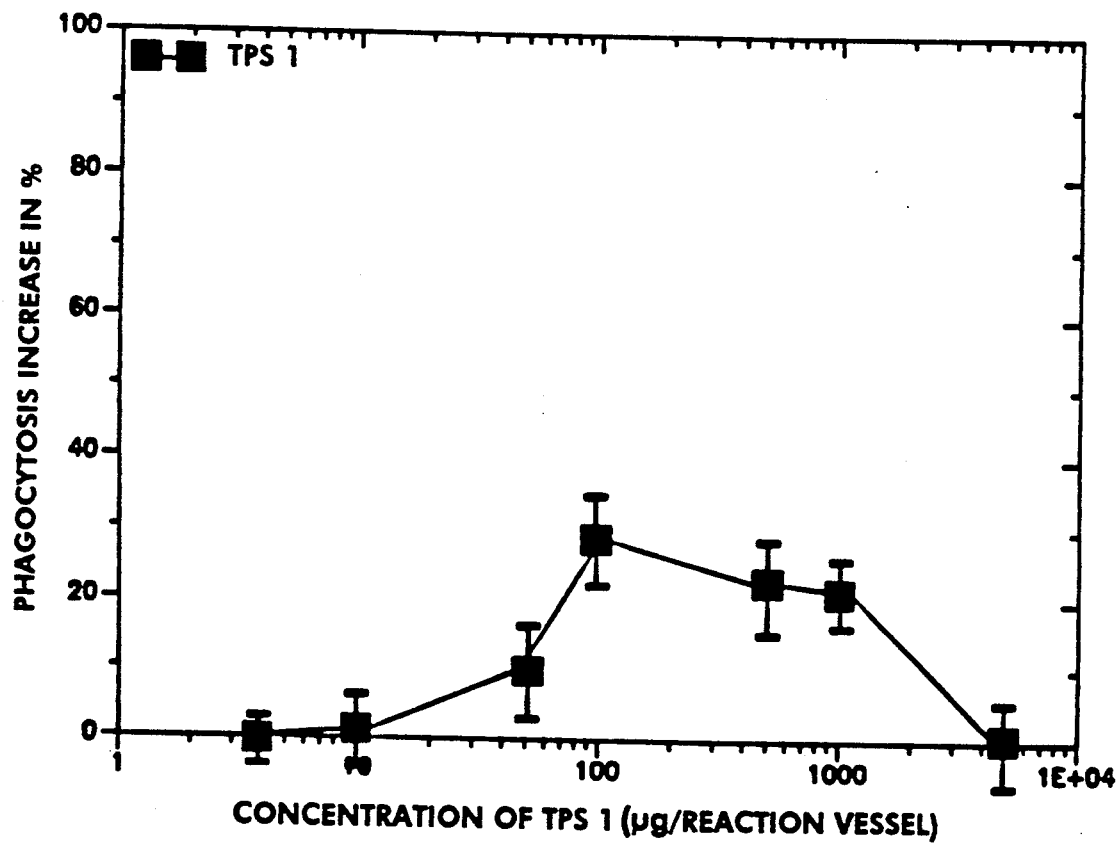
FIG. 7 is a graph showing the results of the phagocytosis assay for neutrophilic granulocytes with TPS 1 as described in Example 6.
Figure 8:
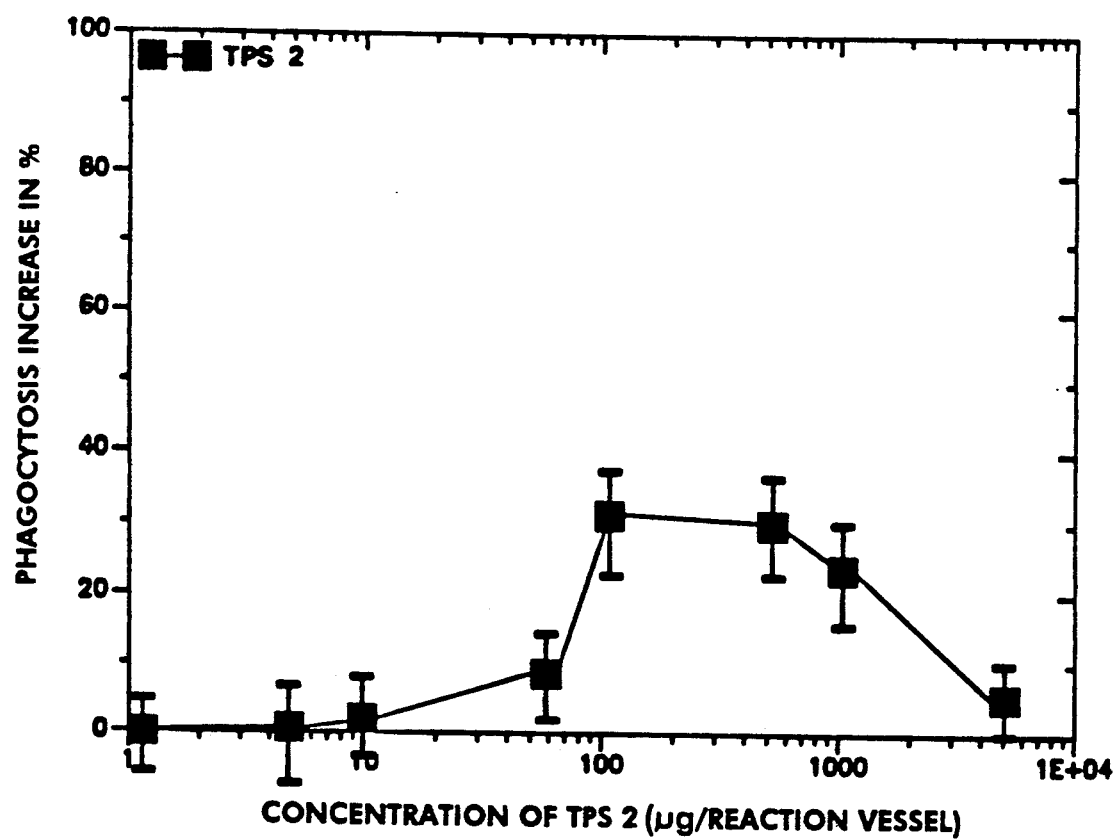
FIG. 8 is a graph showing the results of the phagocytosis assay for neutrophilic granulocytes with TPS 2 using *Candida albicans* as the target cells as described in Example 6.

The results of these tests are reproduced in FIGS. 7 and 8.

EXAMPLE 7

The antiviral effect of TPS against retroviruses was proved in a human in vitro model by two independent test systems.

In the first test system the activity of reverse transcriptase was determined according to the method of B. Broiesz et al., Proc. Natl. Acad. Sci., USA 77, 7415 (1980). The activity of virus-inherent reverse transcriptase serves as an indicator of the virus activity. It is measured by incorporation of dexoxythymidine-5'-triphosphate (TTP) labelled with 3H-methyl.

In the second test system the membrane protein p24 inherent in human retroviruses was determined by an "antigen-capture"-ELISA according to Popovic et al., Science 224, (1984). In this test the stain intensity measured as extinction at 410 nm is proportional to the concentration of the p24 present.

For both test systems, peripheral blood leukocytes infected with HIV-viruses were pre-stimulated for 3 days with TPS and then post-incubated for 11 days with interleukin-2 medium. After 14 days in total the virus titre of the culture supernatants of these peripheral blood leukocytes (PBL), together with that of suitable samples introduced for comparison purposes, was determined using both test processes. The results are reproduced in Tables 1 and 2. They show that TPS, while maintaining the mitogenic properties towards T-helper cells and immature T-cells and zero-cells, has an inhibiting effect on the new infection of the T-helper cells formed by the TPS-effect and at the same time brings about a distinct reduction in the initial concentration of the virus used.

TABLE 1

Reverse Transcriptase Test according to Broiesz et al.

| Test formulation | Activity of the dTdA (DNA-synthesis) as cpm | Activity of the dTrA (RNA-synthesis) as cpm |
|---|---|---|
| PBL infected with 50,000 units of HTLV$_{IIIb}$, without stimulation of growth | 2566 | 1789 |
| PBL not-infected, activated with PHA-P | 2278 | 1868 |
| PBL infected with 50,000 units of HTLV$_{IIIb}$, activated with PHA-P | 3348 | 100445 |
| PBL infected with 50,000 units of HTLV$_{IIIb}$, activated with TPS | 2238 | 2194 |

TABLE 2

Antigen-capture test according to Popovic et al.

| Test formulation | Extinction 410 nm |
|---|---|
| PBL not infected, without growth stimulation | 0.046 |
| PBL not infected, activated with PHA-P | 0.035 |
| PBL not infected, activated with TPS | 0.044 |
| PBL infected with 25000 units of HTLV$_{IIIb}$, without growth stimulation | 0.061 |
| PBL stimulated with PHA-P, infected with 25,000 units of HTLV$_{IIIb}$ | 0.353 |
| PBL stimulated with TPS, infected with 25,000 units of HTLV$_{IIIb}$ | 0.051 |
| PBL without growth stimulation, infected with 50,000 units of HTLV$_{IIIb}$ | 0.059 |
| PBL stimulated with PHA-P, infected with 50,000 units of HTLV$_{IIIb}$ | 0.804 |
| PBL stimulated with TPS, infected with 50,000 units of HTLV$_{IIIb}$ | 0.055 |
| PBL without growth stimulation, infected with 300000 units of HTLV$_{IIIb}$ | 0.256 |
| PBL stimulated with PHA-P, infected with 300,000 units of HTLV$_{IIIb}$ | 2.819 |
| PBL stimulated with TPS, infected with 300,000 units of HTLV$_{IIIb}$ | 0.187 |

EXAMPLE 8

Effect of TPS on concentrated B- and T-lymphocyte fractions concentration of T-cells:

To concentrate T-cells peripheral human blood leukocytes were obtained through a polysaccharose gradient and the monocytic cells removed according to the adherence process of Gartner et al. Science 233, 215 ff. (1986).

the separation process described for mouse spleen cells by Julius et al., Eur. J. Immunol. 3, 6785 ff. (1973) was adapted and used to concentrate T cells.

Concentration of T-cell fractions:

Nylon wool (Leuko-Pak, Fenwall Lb., Derfield, USA) was boiled with re-distilled water 10 times prior to use, to quantitatively remove any interfering water-soluble impurities.

The wool was then dried and stored dust-free. 1 g of the pre-cleaned wool was placed into a 10 ml glass syringe, provided with 5 ml of re-distilled water and then autoclaved so as to produce a separation column.

The prepared column was then equipped with a sterile tap and cannula. After this the column was heated to 37° C., rinsed with 75 ml BSS + 5% AB-serum and incubated for 1 hour at 37° C. with the tap closed. The cell suspension of peripheral human blood leukocytes was prepared as previously indicated. The non-adherent cells were stirred up and centrifuged off. The thus obtained, non-adherent cells were taken up in 2-3 ml of BSS +5% human AB-serum and brought to the column. The charged column was left to stand for 1 hour at 37° C. in the incubator. The cells not adhering to the nylon wool were rinsed away carefully approx. 35 ml of extract being collected. The cells thus obtained were used for test formulations which required concentrated T-cell fractions.

Concentration of B-cell fractions:

B-cell fractions were obtained by subjecting human peripheral blood leukocytes to the polysaccharose gradients of the adherence separation process according to Gartner et al. (loc cit.) and to the treatment described above.

The cells adhering to the nylon column which were not eluted were rinsed away with 25 ml of ice-cold PBS-solution without $Ca^{2+}$ and $Mg^{2+}$.

These cells were used in the test systems as concentrated B-cell fractions.

The effect of TPS on the DNA-synthesis rate is measured by the incorporation of 3H-thymidine. RPMI-1640-medium supplemented with 10% human AB-serum is used as the test medium. Concentrated T- and B-cell fractions and PBL were inoculated in a concentration of $5 \times 10^5$ cells per well to a 96 well flat-bottomed microtitre plate. The autologous monocytes were added a concentration of $5 \times 10^4$ cells to the corresponding samples. TPS was used in an ultimate concentration of 1 mg/ml pe$^-$ well. The plates were incubated for 4 days at 37° C., during the last 12 hours of which 0.5 Ci per well of the microtitre plate were present.

The incorporation rate was then determined according to the process described in Example 3.

Figure 9:
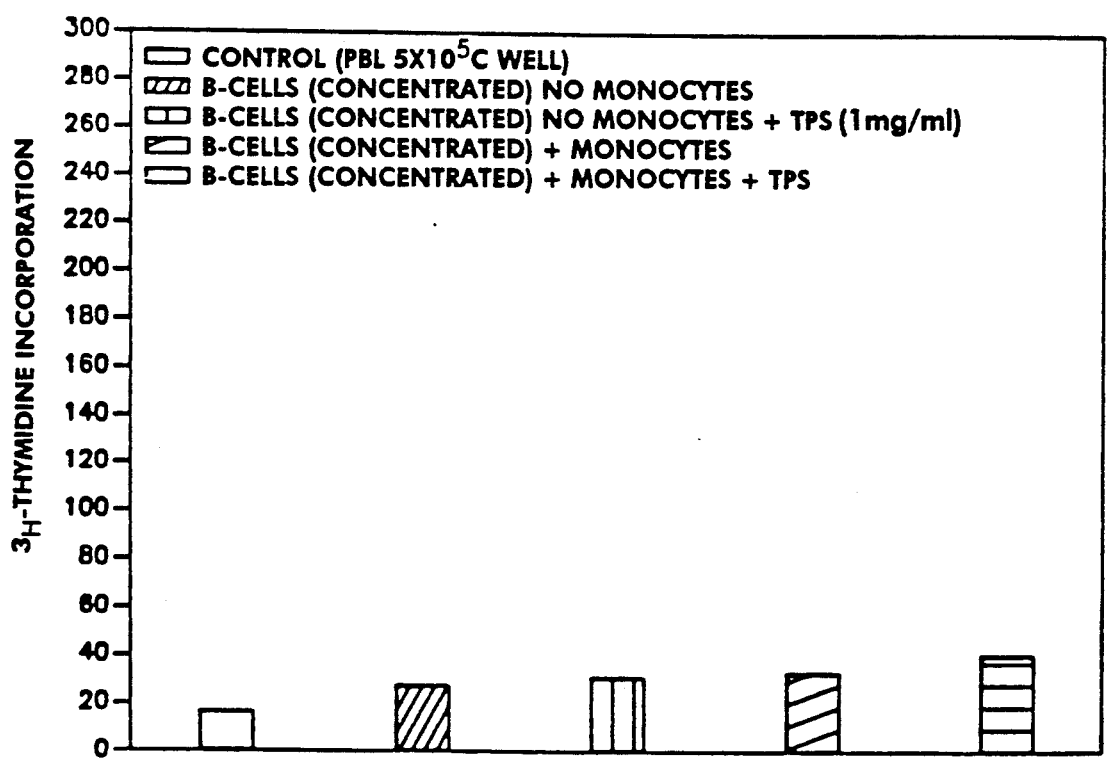
FIG. 9 is a bar graph showing the lack of notable effect of TPS on concentrated B-lymphocyte fractions with and without monocytes as described in Example 8.

The results are reproduced in FIGS. 9 and 10. They show that TPS has no notable effect on concentrated B-lymphocyte fractions, while the T-lymphocytes are selectively stimulated in the presence of monocytes or macrophages. This result confirms the results described in Example 4.

EXAMPLE 9

Examination of interleukin-2 production and the expression of the interleukin-2-receptor as a parameter for T-helper cell activation.

The anti-interleukin-2 test was carried out according to the manufacturer's information sheet of the Company Genzyme Corp., USA, as Interest $2^R$. Cell culture supernatants (conditioned media) of peripheral blood leukocyte fractions, which had been incubated previously for 4 days in DME + 10% AB-serum, were used as the test fraction.

Test procedure:

Two days before the test start the microtitre plate was coated with monoclonal anti-interleukin-2 antibodies. For this purpose the monoclonal antibodies were re-suspended in 11.5 ml of "coating buffer". 100 μl of this solution was distributed per well of a microtitre plate (Genzyme). The plate was then incubated in a humid chamber at 4° C. for the period of time indicated above.

On the day of the test the interleukin-2 standard, consisting of recombinant human Il-2 (rIL-2), was reconstituted with DME + 10% of AB-serum and the following dilution series produced: the lyophilized rIl-2 was taken up in 1 ml of the culture medium. This solution corresponded to an Il-2 concentration of 500 U/ml. 0.1 ml was removed from this solution and it was refilled to 1 ml with "coating buffer".

This process was repeated 3 times in such a manner that 0.1 ml of the previous standard dilution was removed and filled up to 1 ml with "coating buffer". A concentration series of 500 U/ml to 0.5 U/ml rIl-2 was thus obtained.

After coating with rIl-2 this was washed three times with washing buffer. The interleukin-2 standard dilutions were then distributed in duplicates at 100 µl/well of a microtitre plate. 100 µl/well of culture medium, which was incubated under the same conditions as applied to the production of the conditioned media, served as a negative control. The plates were then incubated at 37° C. for one hour and then washed again three times with washing buffer.

In the meantime the second antibody, a polyvalent rabbit anti-human IL-2 antibody, was prepared by mixing 0.3 ml of the antibody solution with 14 ml PBS/Tween washing buffer. This solution was distributed in 100 µl steps per microtitre well. Incubation took place for 1 hour at 37° C.

This was then washed again three times with PBS/Tween washing buffer and incubated with the third antibody. This was a goat anti-rabbit antibody conjugated with alkaline phosphatase. 200 µl of this antibody conjugate was mixed with 12 ml of PBS/Tween washing buffer and distributed at 100 µl/well.

Incubation took place for one hour at 37° C.

After washing three times with PBS/Tween-washing buffer this was incubated for one hour at 20° C., with the substrate which consisted of

| substrate buffer | 6 ml |
|---|---|
| MgCl₂ solution | 6 ml |
| p-NPP-substrate | 10 mg, | which was distributed at 100 µl/well and incubated for one hour at 20° C.

The enzymatic liberation of p-nitrophenol from p-NPP is proportional to the amount of bound interleukin-2.

The quantification of the measurement results was carried out in an ELISA-reader (Dynatech) at a wavelength of 410 nm.

The results are reproduced in Tables 3 and 4 as average values of the respective measurements. They show the TPS-induced increase in interleukin-2 production.

TABLE 3

| Standard dilution for IL-2 Curve standards | | Extinction Controls |
|---|---|---|
| Interleukin-2 | 500 U | 0.667 |
| Interleukin-2 | 50 U | 0.350 |
| Interleukin-2 | 5 U | 0.203 |
| Interleukin-2 | 0.5 U | 0.154 |
| Interleukin-2 | 0.05 U | 0.063 |
| Interleukin-2 | 0 U | 0.003 |

TABLE 4

| Formulation | Extinction | c(U/ml) |
|---|---|---|
| PHA-P (10 µg/ml) | 0.229 | 16.5 |
| TPS (1 mg/ml) | 0.276 | 24.0 |
| Controls (RPMI 1640 + 10% AB-serum) | 0.158 | 0.83 |

EXAMPLE 10

Determination of the action mechanism of TPS:

Interleukin-1 and interferon-gamma are essential cytokines which play a decisive role in the activation of T-cells and monocytes. While interferon-gamma is only produced by activated Tcells, the production of interleukin-1 takes place primarily in monocytes or macrophages. T-cell activation can be almost completely specifically blocked by antibodies against interferon-gamma and interleukin-1 depending on dose. In contract, only a very slight inhibition is comparatively achieved by control antibodies even in very high concentrations.

Procedure:

Peripheral human blood leukocytes were obtained using a polysaccharose gradient and were inoculated in a concentration of $5 \times 10^5$ cells per well of a microtitre plate. TPS was dissolved in DME-medium, supplemented with 10% human AB-serum and used for the test in an ultimate concentration of 1 mg/ml. The activity of TPS was measured using the 3H-thymidine incorporation rate as described in Example 3.

The specific anti-interleukin-1 and gamma-interferon antibodies were obtained from the Genzyme company. They were dialyzed prior to the test start for 48 hours under sterile conditions against distilled water so as to quantitatively remove the preservative sodium acid. The titre of the antibodies was then adjusted to 200 U/100 µl, and the antibodies were used in a titrated ultimate concentration of 100 U/well to 1U/well of a 96-well flat-bottomed microtitre plate in a volume of 100 µl of DME-medium +10% AB-serum. Peripheral blood leukocytes and TPS were added to 50 ul of supplemented DME-medium. The plates were then incubated in the incubator under standard conditions.

The results are reproduced in Table 5 and FIG. 11.

They show that the effect of TPS on PBL can be reduced by high doses of anti-IL-1 and anti-u-IFN. It was in addition possible to prove that this effect was not based on unspecific receptor blocking.

TABLE 5

| Test formulation | cpm |
|---|---|
| PBL + TPS (1 mg/ml) | 145137 +/− 1523 |
| PBL without TPS | 16303 +/− 534 |
| PBL + 100 U anti-IL-1 without TPS | 27069 +/− 749 |
| PBL + 100 U anti IL-1 + TPS (1 mg/ml) | 33047 +/− 871 |
| PBL + 10 U anti-IL-1 + TPS (1 mg/ml) | 49985 +/− 1003 |
| PBL + 1 U anti-IL-1 + TPS (1 mg/ml) | 82913 +/− 1324 |
| PBL + 100 U anti-interferon-gamma without TPS | 37738 +/− 656 |
| PBL + 100 U anti-interferon-gamma + TPS (1 mg/ml) | 43875 +/− 637 |
| PBL + 10 U anti-interferon-gamma + TPS (1 mg/ml) | 46726 +/− 527 |
| PBL + 1 U anti-interferon-gamma + TPS (1 mg/ml) | 78681 +/− 799 |

TABLE 5-continued

| Test formulation | cpm |
| --- | --- |
| PBL + mouse-IgG + TPS (1 mg/ml) | 100807 +/− 1956 |
| PBL + IgG-fraction human + TPS (1 mg/ml) | 107765 +/− 2097 |

EXAMPLE 11

Determination of the in vivo immunoregulatory effect of TPS on BALB-C-inbred mice The test was carried out following Moore et al. (M.A.D. Moore, "Stolman Lecture", "Modern Trends of Human Leukemia", Wilsede (1988), Springer Verlag in press). 10 BALB-C-mice were grouped together into a collective and treated either intravenously with 0.5 ml RPMI 1640 medium or with TPS, dissolved in RPMI 1640 medium, end concentration 1 mg/500 ul/animal. Five animals of the TPS group and of the RPMI 1640 control group were irradiated with a sublethal dose of 600 rad from a cobalt bomb. The blood of each animal was taken by puncture of the retro-orbital venous plexus before the treatment so as to determine normal values, and after treatment with TPS or with medium and after irradiation. The leukocyte count per nl was then determined from the blood thus obtained with the aid of a Neubauer chamber, in which the red blood corpuscles were destroyed by treatment with gentian violet and the number of leukocytes was determined by counting out of the chamber. The results are reproduced in FIG. 12. They show that a TPS-determined increase in the leukocyte count in comparison with the RPMI 1640 standard also occurs in vivo. The group of mice treated with TPS also have a higher leukocyte count after sublethal irradiation than the control group treated with RPMI.

We claim:

1. A medicament having mitogenic activity containing, together with a pharmaceutically acceptable carrier, a component extracted form thuja plants, which contains polysaccharides, which is obtained by:
   (a) extracting the crushed, above-ground plant parts, which have been cleaned with organic solvents, with an alkaline-aqueous solvent,
   (b) mixing the extract with an organic solvent, to precipitate polysaccharides and proteins from the extract,
   (c) separating the precipitate and dissoluting the precipitate in water at a temperature below ambient temperature,
   (d) acidifying the solution to precipitate the proteins,
   (e) separating the percipitate and mixing the supernatant with an organic solvent, and
   (f) dialyzing the percipitate and thereafter drying the precipitate.

2. The medicament according to claim 1, wherein the molecular weight of the component is at least 100 D.

3. The medicament according to claim 1, wherein the molecular weight of the component according to ultrafiltration is at lest 100,000 D.

4. The medicament according to claim 1, wherein the component containing the polysaccharide originates from *Thuja occidentalis L.*

* * * * *